United States Patent [19]
Burgio et al.

[11] Patent Number: 4,462,402
[45] Date of Patent: Jul. 31, 1984

[54] METHOD AND ANCHOR FOR ANCHORING

[75] Inventors: Paul A. Burgio, Roseville, Minn.; Derrick A. Jones, Houlton, Wis.; Allen J. Abel, Roseville, Minn.

[73] Assignee: Minnesota Mining and Manufacturing Company, Saint Paul, Minn.

[21] Appl. No.: 441,944

[22] Filed: Nov. 15, 1982

[51] Int. Cl.³ .......................... A61N 1/04; A61F 11/00
[52] U.S. Cl. ................................. 128/303 R; 128/785; 128/784; 128/DIG. 26
[58] Field of Search ............... 128/303 R, 419 R, 784, 128/785, 746, 92 BA, 92 BB, 92 BL, 92 B, 339, 419 P, DIG. 26; 43/772, 44.2, 42.24, 43.16

[56] References Cited

U.S. PATENT DOCUMENTS

| | | |
|---|---|---|
| 3,449,768 | 6/1969 | Doyle. |
| 3,752,939 | 8/1973 | Bartz ............................ 179/107 R |
| 4,276,882 | 7/1981 | Dickhudt et al. ............... 128/419 P |

FOREIGN PATENT DOCUMENTS

| | | |
|---|---|---|
| 2068 | 11/1978 | European Pat. Off.. |
| 76069 | 9/1982 | European Pat. Off.. |
| 2353055 | 9/1952 | Fed. Rep. of Germany. |
| 2823798 | 9/1979 | Fed. Rep. of Germany. |
| 2061733 | 9/1980 | United Kingdom. |

Primary Examiner—Lee S. Cohen
Assistant Examiner—Steven Falk
Attorney, Agent, or Firm—Donald M. Sell; James A. Smith; William L. Huebsch

[57] ABSTRACT

A method for implanting electrodes in or around a human cochlea that involves inserting one end of an anchor in the temperal bone, and functionally engaging a lead to the electrode with the anchor. Numerous anchor embodiments are described together with tools for inserting some of the anchors.

4 Claims, 16 Drawing Figures

METHOD AND ANCHOR FOR ANCHORING

TECHNICAL FIELD

The present invention relates to methods and devices used in implanting electrodes in or around the human cochlea.

BACKGROUND ART

Several methods have been developed to electrically stimulate nerve fibers in the cochlea of a deaf person in a pattern roughly corresponding to longitudinal mechanical waves produced in the environment (which waves are heard as sound by persons with normal hearing) to thus produce the sensation of sound in the deaf person. The details and results of one such method are set forth in a document entitled "Cochlear Implants: Progress and Perspectives" edited by William F. House and Karen I. Berliner, and which is Supplement 91-Volume 91, Mar.-Apr. 1982, No. 2, Part 3 of the Annals of Otology, Rhinology and Laryngology, published by The Annals Publishing Company, 4949 Forest Park Blvd., St. Louis, Mo. 63108, copyright 1982, the content whereof is hereby incorporated herein by reference.

Generally such methods involve implanting an internal electromagnetic coil connected by leads to active and ground electrodes under the skin covering the person's skull and positioning the electrodes at predetermined locations in or adjacent the cochlea. An externally worn adjustable transducer is then used to produce electrical signals in response to longitudinal mechanical waves produced in the environment and received via a microphone on the device, and to couple those electrical signals to an external electromagnetic coil positioned on the outside of the skin opposite the coil under the skin. Electrical signals corresponding to those produced by the transducer are produced in the internal coil by magnetic coupling between the coils, and those signals stimulate the cochlea via the electrodes. While the signals do not produce the same sound sensations from the mechanical waves that the waves produce via the normal human ear, they do produce a range of sound sensations that, with training, can be used by the person to help identify the source of the waves and in many cases to help the person understand human speech.

Implanting the coil with its leads and electrodes under the skin covering the person's head generally comprises (1) exposing the outer surface of the person's temporal bone behind the ear, which is typically done by cutting an arcuate slit in the skin, muscle, and other tissue overlaying that bone, separating, and laying back the flap thus produced; (2) making an opening in the temporal bone through the mastoid and facial recess portions of the temporal bone between the outer surface of the temporal bone and the round window in the cochlea; (3) forming a recess for the coil via a surgical drilling device in the exposed squamous portion of the temporal bone; (4) locating and attaching the internal coil in the recess; (5) positioning the ground electrode in the eustachian tube or some other location such as the opening in the mastoid or under the temporalis muscle; (6) positioning the lead terminating at the active electrode through the surgically prepared opening with the electrode at a predetermined position relative to the cochlea (e.g., which position may be at the outside surface of the round window of the cochlea or inside the cochlea with the lead passing through the round window); (7) anchoring the leads in place through the use of an acceptable adhesive or by packing tissues from the head around them in the opening; and (8) then replacing the flap of skin, muscle, and other tissues by suturing it in place over the coil and opening, and allowing the slit that formed the flap to heal.

Other similar methods have involved the use of a plurality of leads which terminate at spaced active electrodes adapted to be inserted into the cochlea through the round window under the theory that selective activation of the electrodes may selectively stimulate different nerves in the cochlea and result in better sound discrimination by the person.

The use of any such method has presented the problem of properly positioning the electrodes with respect to the cochlea and holding the electrodes in that desired position. Experience has shown that positioning of the active electrode has often disrupted the delicate soft tissues of the cochlea (e.g., the basilar membrane or spiral ligament), and that a positioned electrode is sometimes inadvertently moved from the desired position during the operation. Also, it is sometimes necessary to replace the internal coil during a revision surgery which is done by again making an arcuate incision and folding back a flap of skin, muscle, and other tissues from over the internal coil, cutting the lead or leads connected to the internal coil, reconnecting a new internal coil, and suturing the flap in place over the new internal coil. Inadvertent movement of the electrodes has occurred during such severing and reconnecting of the leads which can result in damage to the cochlea or an improper new position for the electrodes. Such movement occurs because the anchor tissues packed around the leads do not attach firmly to the lead, and because of the slight force necessary to move the leads.

DISCLOSURE OF THE INVENTION

The present invention provides an effective method for positioning one or more of electrodes while they are being implanted through a surgically prepared opening in the temporal bone as described above, and for anchoring those electrodes in place to maintain their position both during the operation by which they are implanted and thereafter, including during changing of the internal coil should that occur.

According to the present invention there is provided an improvement in the method of implanting one or more electrodes in or adjacent the human cochlea, which electrode affords electrical stimulation of nerve fibers to produce the sensation of sound by positioning a lead terminating at the electrode through an opening surgically made in the temporal bone and with the electrode at a predetermined position relative to the cochlea (e.g., within the cochlea or closely adjacent to its round window). The improved method includes (1) providing an anchor having a first end portion, and having a second end portion comprising means for engaging a portion of the lead to restricts longitudinal, transverse and rotational movement thereof relative to the anchor; (2) forming a socket from the opening into the temporal bone, which socket is adapted to receive and hold the first end portion of the anchor; (3) inserting the first end portion of the anchor in the socket; and (4) engaging a portion of the lead with the means for engaging of the anchor to thereby restrict longitudinal, transverse and rotational movement of the electrode.

It has been found that the method has particular advantages where the steps of inserting the first end portion of the anchor in the socket and engaging a portion of the lead with the second end portion of the anchor are performed prior to final positioning of the electrode relative to the cochlea, and where the positioning step includes the step of pulling the lead (which typically has a diameter of about 0.035 inch or 0.09 cm) through the anchor against the frictional engagement of its second end portion to provide such final positioning. Such pulling of the lead (which may be done with a pliers-like instrument such as a forceps) facilitates accurate positioning of the electrode by aligning parts of or indicating marks on the lead with respect to anatomical structures (such as the round window), thereby restricting damage to the delicate cochlear tissues by improper positioning of the electrode.

One anchor adapted to be inserted in the temporal bone and to be engaged with one or more leads extending to an electrode to help position and retain the electrode at a desired location relative to the cochlea comprises: (1) a metal wire having a first end portion of a size capable of insertion inserted in a socket in the temporal bone and comprising means adapted to firmly engage the walls defining the socket, and an opposite generally U-shaped end portion; and (2) a layer of resiliently elastic polymeric material over the adjacent surfaces of the U-shaped end portion, the adjacent surfaces of the layer of polymeric material being spaced to frictionally receive a portion of the lead therebetween, and the layer being sufficiently thick to insure proper electrical insulation between the wire and the lead.

Preferably the first end portion of the anchor includes a barb projecting along one side and toward the second portion of the anchor, and the socket is sized so that its walls will resiliently deflect the barb toward the rest of the first end portion when the first portion is inserted in the socket. The first end portion of the anchor is preferably inserted in the socket when the anchor is rotated from its desired orientation (e.g., by about 90 degrees), and the anchor is then rotated to its desired orientation. This will cause the barb to move out of alignment with any groove it formed in the wall defining the socket as it was inserted to thereby enhance its holding power in the bone, which holding power is produced by pressure applied to the walls defining the socket by the resiliently deflected barb.

While the anchor described above is preferred because of its ease of insertion in the temporal bone and the ease with which the leads may be engaged with it, many other anchor forms described hereinafter also may be found useful, such as bone screws with specially formed transverse slots in their heads.

Also, novel insertion tools have been found useful to facilitate inserting the various anchors in the temporal bone. Such tools are each adapted to releasably engage one form of the anchor so that the anchor can be inserted in the socket by manual manipulation of the tool without the probability that the anchor will be prematurely disengaged from the tool and lost in the recesses of the head, and the tool is adapted to be easily disengaged from the anchor after its insertion in the socket.

BRIEF DESCRIPTION OF DRAWING

The present invention will be further described with reference to the accompanying drawing wherein like numbers refer to like parts in the several views and wherein.

DETAILED DESCRIPTION

Figure 1:
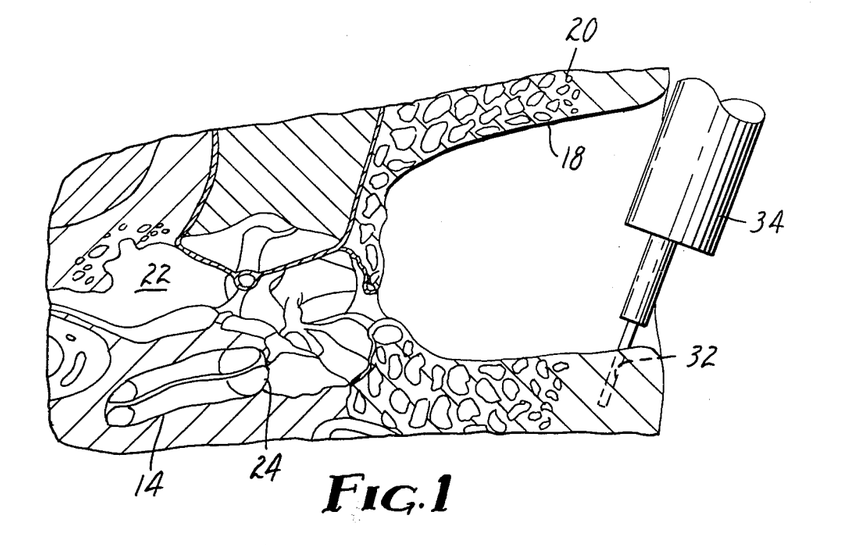
FIGS. 1, 2 and 3 are fragmentary sectional views of the temporal bone and adjacent structures in a human skull illustrating certain steps used to position an electrode included in a method according to the present invention.
Figures 2, 4:
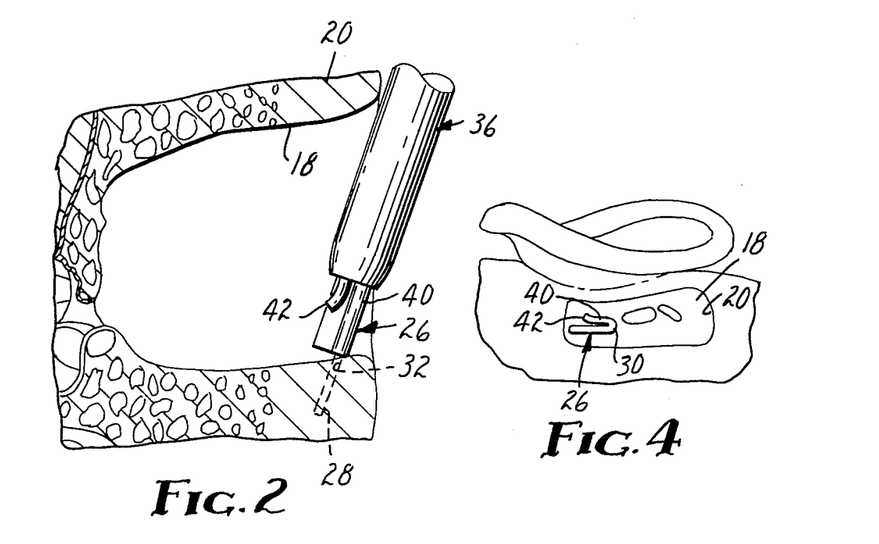
FIGS. 4 and 5 are fragmentary side views, partially in section, of the human skull shown in FIGS. 1, 2 and 3 which also illustrates steps in the method according to the present invention.
Figure 3:
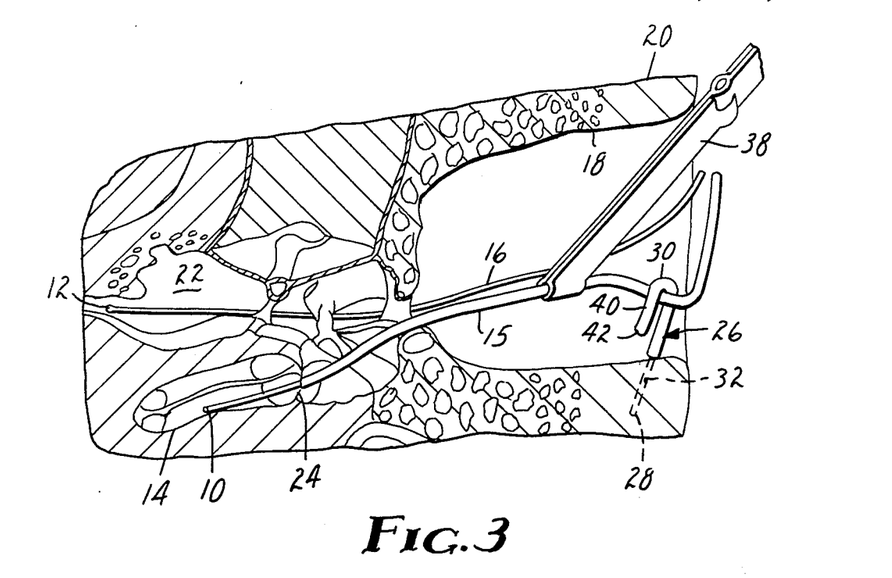
Figure 5:
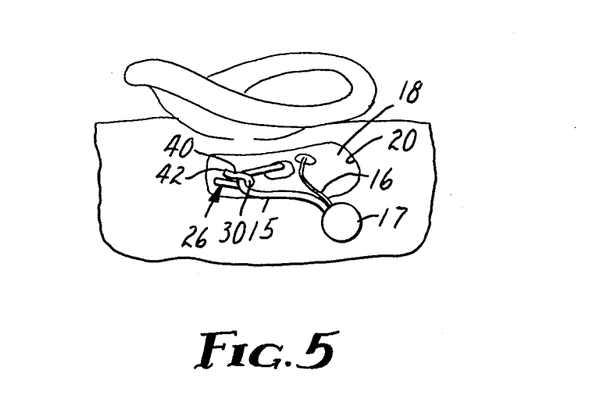

Referring now to FIGS. 1 through 5 there are illustrated steps of an improved method according to the present invention for implanting an active electrode 10 and a ground electrode 12 in or adjacent a human cochlea 14 (which electrodes 10 and 12 afford electrical stimulation of nerve fibers to produce the sensation of sound), by positioning leads 15 and 16 between an electromagnetic coil 17 and the electrodes 10 and 12 through an opening 18 surgically made in a temporal bone 20 and positioning the electrodes 10 and 12 at predetermined positions relative to the cochlea 14 (e.g., such as with the active electrode 10 within the cochlea 14 and the ground electrode 12 within the eustachian tube 22 as illustrated, or alternately (not shown) with the active electrode 10 at a round window 24 of the cochlea 14). The improved method includes (1) providing an anchor 26 (FIG. 5) having a first end portion 28 and having an opposite second end portion 30 adapted to frictionally engage a portion of one or both of the leads 15 and 16 and restrict longitudinal, transverse and rotational movement thereof relative to the anchor 26; (2) forming a socket 32 (as with a surgical drill 34 as is shown in FIG. 1) from the opening 18 into the temporal bone 20, which socket 32 is adapted to frictionally receive the first end portion 28 of the anchor 26; (3) inserting the first end portion 28 of the anchor 26 in the socket 32 (FIG. 4) which may be done through the use of an insertion tool 36 as is shown in FIG. 2 or otherwise; and (4) engaging a portion of one or both of the leads 15 and 16 with the second end portion 30 of the anchor (FIGS. 3 and 5).

Preferably the method is performed by inserting the first end portion 28 of the anchor 26 in the socket 32, and engaging a portion of the lead 15 or 16 with the second end portion 30 of the anchor 26 prior to final positioning of the electrode 10 or 12, and then positioning the lead 15 or 16 with the electrode 10 or 12 at its final predetermined position relative to the cochlea 14, with the positioning step comprising the step of pulling the lead 15 or 16 through the anchor 26 as with a forceps 38 against the frictional engagement of the second end portion 30 of the anchor 26 with the lead 15 or 16 (FIG. 3) to achieve the final positioning of the electrode 10 or 12. It has been found that such pulling of the lead 15 or 16 through the anchor facilitates accurate positioning of the electrode 10 or 12 by aligning parts of or indicating marks on the leads 15 or 16 with respect to anatomical structures (such as the round window 24), thereby restricting damage to the delicate tissues of the cochlea 14 by improper positioning of the electrode 10 or 12.

Figure 6:
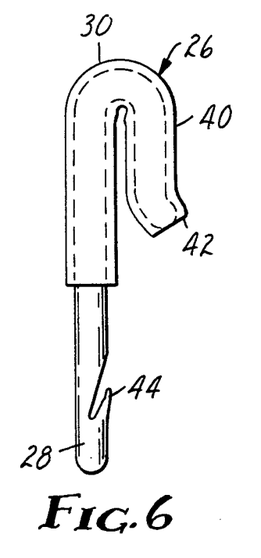
FIG. 6 is an enlarged side view of an anchor which is shown being inserted or shown in place in FIGS. 2, 3, 4 and 5.

As is best seen in FIG. 6, the anchor 26 adapted to be inserted in the temporal bone 20 and to engage with one or both of the leads 15 or 16 to help position and retain the electrode 10 or 12 at a desired location relative to the cochlea 14 comprises: (1) a metal wire (e.g., of commercially pure titanium, 0.038 inch or 0.096 cm in diameter) providing the first end portion 28 adapted to be inserted in the socket 32 in the temporal bone 20, and the opposite second end portion 30 which is generally U-shaped; and (2) a resiliently elastic polymeric tube 40 (e.g., medical-grade silastic tubing with a wall thickness of about 0.017 inch or 0.043 cm) over the U-shaped second end portion 30 which provides a layer of the polymeric material over the adjacent surfaces of the wire along its U-shaped end portion 30, with the adjacent surfaces of the layer or tube 40 being spaced to frictionally receive a portion of the lead 15 or 16 therebetween. The layer or tube 40 thus serves both to frictionally hold the lead 15 or 16 in place while affording longitudinal movement of the lead 15 or 16 under a force applied by the forceps 38, and also helps to electrically insulate the lead 15 for the active electrode 10 from the metal wire part of the anchor 26.

The distal tip 42 of the second U-shaped end portion 30 preferably diverges away from its proximal end to afford pressing or pulling the lead therebetween. The anchor 26 is adapted so that when its first end portion is engaged in the socket 32, the distal tip 42 can be spaced from the temporal bone 20 so that the space between the temporal bone 20 and the distal tip 42 and the space between the adjacent surfaces of the tube 40 over the second end portion 30 provide, in combination, a generally L-shaped space adapted to receive a portion of the lead 15 or 16. This L-shaped space includes an outer portion between the temporal bone 20 and distal tip 42 which will help to initially locate the lead 15 or 16 adjacent the anchor 26 and an inner portion between the adjacent walls of the tube 40 in which the lead 15 or 16 can be frictionally held.

Also, the first end portion 28, as illustrated, has a barb 44 which provides means adapted to firmly engage the walls defining the socket 32. The barb 44 is formed by slotting the first end portion 28 at an acute angle to its axis (e.g., as with a 0.006 inch wide slot formed by electro discharge machining) and bending the tip of the triangular part thus formed away from the rest of the first end portion 28 to provide the barb 44 which projects along one side of the first end portion 28 and toward the second end portion 30 of the anchor 26. The barb 44 projects sufficiently (e.g., 0.006 inch or 0.015 centimeters) that it can be resiliently deflected toward the rest of the first end portion 28 by the walls of the socket 32 in which it is inserted, and may be formed with a rounded tip so that the anchor 26 can be pulled from the socket 32 without the danger of breaking off the tip of the barb 44 or part of the first end portion 28.

Figure 7:
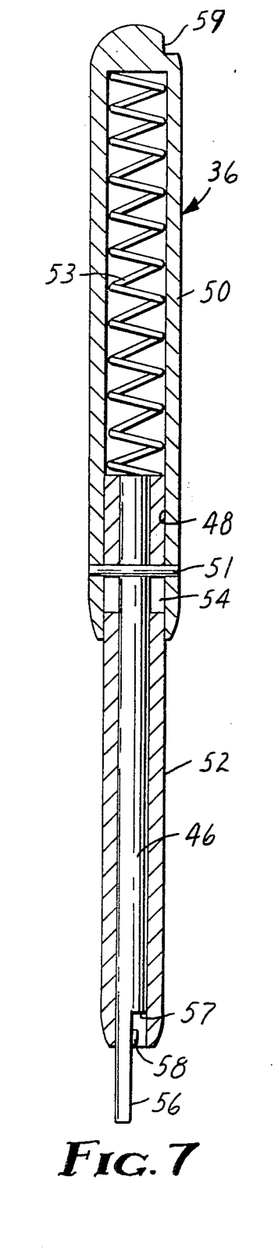
FIG. 7 is an enlarged sectional view of an insertion tool for use in inserting the anchor of FIG. 6 and which is shown being used in FIG. 2.

The insertion tool 36 adapted to insert the anchor 26 is best seen in FIG. 7. As illustrated, the tool 36 comprises a mostly cylindrical blade 46 having a central axis and one end portion that projects into and is fixed within a socket 48 in a handle 50 by a pin 51. A hollow tubular sleeve 52 is mounted for axial sliding movement along the blade 46 from (1) an outer engage position to which the sleeve 52 is biased by a spring 53 between the sleeve 52 and the handle 50 at the bottom of the socket 48 (FIGS. 2 and 7); and (2) a release position (not shown) with the sleeve 52 telescoped farther within the socket 48, which engage and release positions are defined by the engagement of the pin 51 at opposite ends of opposed axially extending slots 54 in the sleeve 52. An end drive portion is provided at the end of the blade 46 opposite the handle 50. The end drive portion has a planar axially extending side surface 56, a radially extending pressure surface 57, and a lug 58 projecting from the side surface 56. The surfaces 56 and 57 and lug 58 are sized and spaced so that either side surface of the anchor 26 may be positioned against the side surface 56 of the blade 46 with the first end portion 28 of the anchor 26 projecting axially away from the distal end of the blade 46, an end surface of the second end portion 30 opposite the first end portion 28 abutting the pressure surface 57, and with the lug 58 received in the transverse opening through the second end portion 30 of the anchor 26 between the adjacent surfaces of the tube 40. In this position side or drive surfaces of the lug 58 aligned axially of the blade 46 are in engagement with adjacent spaced side surfaces of the tube 40 of the anchor 26 and can transfer torque thereto when the handle 50 is rotated about its axis. Also, a retaining surface of the lug 58 opposite the pressure surface 57 is adjacent a support surface of the anchor 26 on the side of the tube 40 opposite the end surface of the second end portion 28 to retain the part of the anchor second end portion 28 therebetween. When the sleeve 52 is in its engage position it will project over the lug 58 and partially along the second end portion 30 of the anchor 26 so that the second end portion 30 of the anchor 26 will be retained on the tool 36 by the surfaces 56, 57, lug 58 and inner surface of the sleeve 52 (FIG. 2). When the sleeve 52 is moved to its release position against the bias of the spring 53, however, it retracts from over the lug 58 so that the lug 58 can be withdrawn from within the opening in the second end portion 30 of the anchor 26 to release the insertion tool 36 from the anchor 26.

To use the insertion tool 36, the sleeve 52 is moved to its release position, the anchor 26 is positioned along the side surface 56 with the lug 58 within its U-shaped second end portion 30, and the sleeve 52 is allowed to move to its engage position under the influence of the spring 53. The tool 36 can then be used to press the projecting first end portion 28 of the anchor 26 into the socket 48, with force applied to the tool 36 being transferred to the anchor 26 through the pressure surface 57, and to rotate the anchor to a desired location (indicated by a position indicating notch 59 across the end of the handle 50) with rotational force being applied to the anchor 26 via the lug 58 and the side surface 56. After the anchor 26 is in place, the sleeve 52 can again be moved to its release position and the lug 58 moved sideways from within the U-shaped second end portion 30 of the anchor 26 to remove the tool 36 from the inserted anchor 26.

Figure 8:
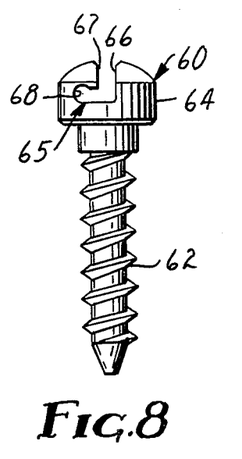
FIG. 8 is a side view of a first alternate embodiment of an anchor which may be used in the method according to the present invention.

FIG. 8 illustrates a first alternate embodiment of an anchor that could be used in the method according to the present invention, generally designated by the reference numeral 60. The anchor 60 is a screw-like member, made by modifying a standard bone screw, which comprises a threaded first end portion 62 adapted to be inserted in a socket in a temporal bone; and a head 64 defining a second end portion of the anchor 60. The head 64 has a transverse opening or slot 65, modified by cutting via electro-discharge machining, which slot includes an outer axially aligned portion 66 having an inlet opening 67 extending across the head 64, and an inner portion 68 extending generally at a right angle to the outer portion 66. The outer slot portion 66 has arcuate walls and a width adapted to receive a lead with light friction between the arcuate walls and the lead to facilitate moving the lead to position it after the lead is engaged in the outer slot portion 66, whereas the inner slot portion 68 is sized to firmly frictionally engage the lead to hold it in place. Thus an electrode at the end of the lead may be positioned while the lead is in the outer slot portion 66, and then pushed into the inner slot portion 68 to hold it in place. The head 64 may be coated with a suitable insulating material (such as a polymer) to help frictionally hold the lead and to help electrically insulate the wire in the lead, or may be entirely formed of polymeric material.

Figure 9:
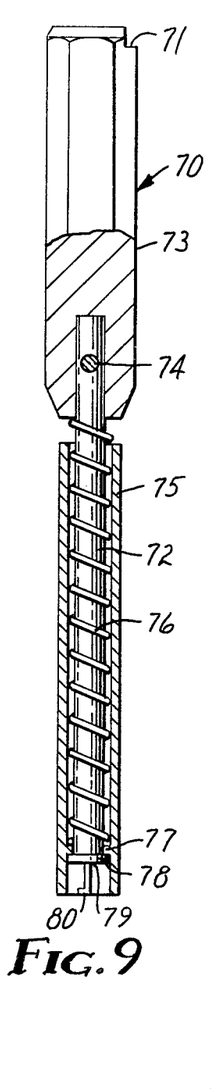
FIG. 9 is an enlarged sectional view of a first alternate embodiment of an installation tool for use with the anchor shown in FIG. 8.

An insertion tool 70 adapted to insert the anchor 60 is best seen in FIG. 9. As illustrated, the tool 70 comprises a blade 72 having a central axis and one end portion that projects into and is fixed within a socket in a handle 73 by a pin 74. A tubular sleeve 75 is mounted for axial sliding movement along the blade 72 from (1) an outer engage position to which the sleeve 75 is biased by a spring 76 around the blade 72 between an inwardly projecting lip 77 on the sleeve 75 and the handle 73 with the lip 77 abutting an outwardly projecting flange 78 on the blade 72; and (2) a release position with the sleeve 75 abutting the handle 73. And end drive portion is provided at the end of the blade 72 opposite the handle 73. The end drive portion has an end pressure surface 79 adapted to engage the end surface on the head 64 of the anchor 60, and a generally L-shaped projecting drive lug 80 adapted to slide transversely into the opening of slot 65 in the head 64 with the threaded end portion 62 of the anchor 60 projecting axially away from the pressure surface 79 of the blade 72. In this position side or drive surfaces of the lug 80 aligned axially of the blade 72 are in engagement with adjacent side surfaces defining the slot 65 in the head 64 of the anchor 60 and can transfer torque thereto as the handle 73 is rotated about its axis. Also, a retaining surface of the lug 80 opposite the pressure surface 79 is adjacent a support surface of the anchor 60 on the side of the part of the head 64 opposite its end surface to retain that part of the head 64 therebetween. When the sleeve 75 is in its engage position it will project over the lug 80 and along the sides of the head 64 of the anchor 60 when it is positioned with the L-shaped lug 80 in its slot 65 so that the anchor 60 will be retained on the tool 70 via the lug 80 and the sleeve 75. When the sleeve 75 is moved to its release position against the bias of the spring 76, however, it retracts from over the head 64 of the anchor 60 so that the lug 80 can be slid transverse of the anchor 60 from within the head 64 of the anchor 60 to release the insertion tool 70 from the anchor 60.

To use the insertion tool 70, the sleeve 75 is moved to its release position, and the head 64 of the anchor 60 is slid transversely over the lug 80 with the lug 80 in the slot 65 until the head 64 is centered on the surface 79. The sleeve 75 is then allowed to move to its engage position under the influence of the spring 76. The tool 70 can then be used to rotate the projecting threaded first end portion 62 of the anchor 60 into a socket with the lug 80 acting as a screwdriver blade to transfer rotational force from the tool 70 to the anchor 60. After the anchor 60 is in place with the slot 65 properly aligned (which can be determined by the alignment of a position indicating notch 71 across the end of the handle 73), the sleeve 75 can be moved to its release position and the lug 80 can be slid sideways from within the slot 65 in the head 64 to release the tool 70 from the inserted anchor 60.

Figure 10:
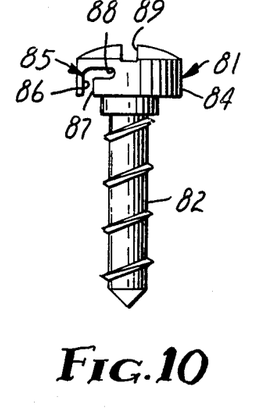
FIG. 10 is a side view of a third alternate embodiment of an anchor which may be used in the method according to the present invention.

FIG. 10 illustrates a third alternate embodiment of an anchor 81 according to the present invention, which, like the anchor 60, is a screw-like member made by modifying a standard bone screw, and which comprises a threaded first end portion 82 adapted to be inserted in a socket in a temporal bone; and a head 84 defining a second end portion of the anchor 81. The head 84 has a transverse slot 85 made by cutting via an electron emission machine and which, like the slot 65 in the anchor 60, includes an outer axially parallel portion 86 having an inlet opening 87 extending across the head 84, and an inner portion 88 extending generally at a right angle to the outer portion 86, which portions 86 and 88 provide essentially the same functions as the inner and outer portions 68 and 66 of the slot 65 in the anchor 60. Unlike the slot 65 in the anchor 60, however, the slot 85 is cut into the head 84 from its surface adjacent the threaded end portion 82. The anchor 80 thus must be inserted by standard screw driving equipment via a conventional screw-driver receiving slot 89.

Figure 11:
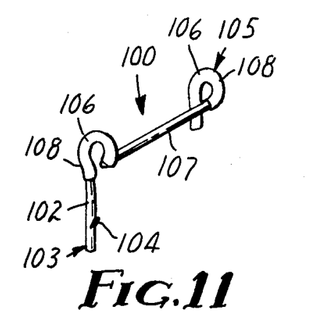
FIG. 11 is a side view of a fourth alternate embodiment of an anchor which may be used in the method according to the present invention.

FIG. 11 shows a fourth alternate embodiment of an anchor that can be used in the method according to the present invention generally designated by the reference numeral 100. The anchor 100 is particularly adapted for use with leads that benefit from support adjacent both ends of an opening formed in a temporal bone between its surface and the round window of a cochlea, as the anchor 100 is adapted to engage the lead at two spaced positions. The anchor comprises a metal wire 102 having a first end portion 103 formed with a barb 104 and adapted to be inserted in a socket in a temporal bone, and a second end portion 105 adapted to engage portions of a lead. The second end portion 104 comprises first and second spaced generally inverted U-shaped parts 106 positioned with the major planes of the U-shaped parts 106 generally parallel, and a connecting part 107 connecting ends of the U-shaped parts 106 that extends generally at right angles to the planes of the U-shaped parts 106. The first end portion 103 projects from the end of one of the U-shaped parts 106 opposite the connecting part 107. Resiliently elastic polymeric tubes 108 are positioned over the wire 102 around the U-shaped parts 106, with the adjacent surfaces of the tubes 108 spaced to frictionally receive portions of a lead therebetween.

Figure 12:
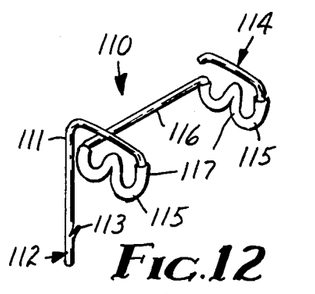
FIG. 12 is a side view of a fifth alternate embodiment of an anchor which may be used in the method according to the present invention.

FIG. 12 shows a fifth alternate embodiment of an anchor according to the present invention generally designated by the reference numeral 110. The anchor 110, like the anchor 100, is also particularly adapted for use with leads that benefit from support adjacent both ends of an opening formed in a temporal bone between its outer surface and the round window or oval window of a cochlea, as the anchor 110 is adapted to also engage the leads at two spaced positions. The anchor 110 comprises a metal wire 111 having a first end portion 112 formed with a barb 113 and adapted to be inserted in a socket in a temporal bone, and a second end portion 114 adapted to engage portions of two leads. The second end portion 114 comprises first and second spaced parts 115 which are generally in the shape of two adjacent U's or W-shaped and are positioned with the major planes of the W-shaped parts 115 generally parallel, and a connecting part 116 connecting ends of the W-shaped parts 115 that extends generally at right angles to the planes of the W-shaped parts 115. The first end portion 112 projects from the end of one of the W-shaped parts 115 opposite the connection part 116. Resiliently elastic polymeric tubes 117 are positioned over the wire 112 around the W-shaped parts 115, with the adjacent surfaces of the tubes 117 spaced to frictionally receive portions of the leads therebetween.

Figure 13:
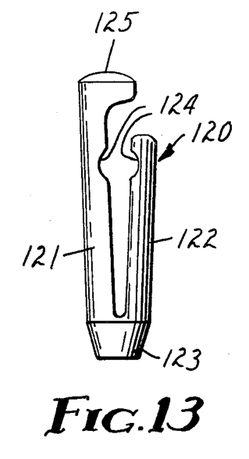
FIG. 13 is a side view of a sixth alternate embodiment of an anchor which may be used in the method according to the present invention.

FIG. 13 illustrates a sixth alternate embodiment of an anchor 120 which may be used in the method according to the present invention. The anchor 120 is a generally U-shaped member of metal or a suitable polymeric material comprising two leg portions 121 and 122 joined at an apex 123, which anchor 120 is resiliently bendable at the apex 123. The U-shaped member has transverse notches 124 along opposing surfaces of the leg portions 121 and 122 adapted to receive and retain a lead therebetween. The anchor 120 may be inserted apex 123 first into a socket in a temporal bone so that the walls of the socket press the leg portions 121 and 122 together and against a lead in the notches 124 to frictionally retain the lead therebetween. The distal end 125 of the leg 121 is enlarged and adapted to receive force to drive the anchor 120 into a socket.

Figures 14, 15:
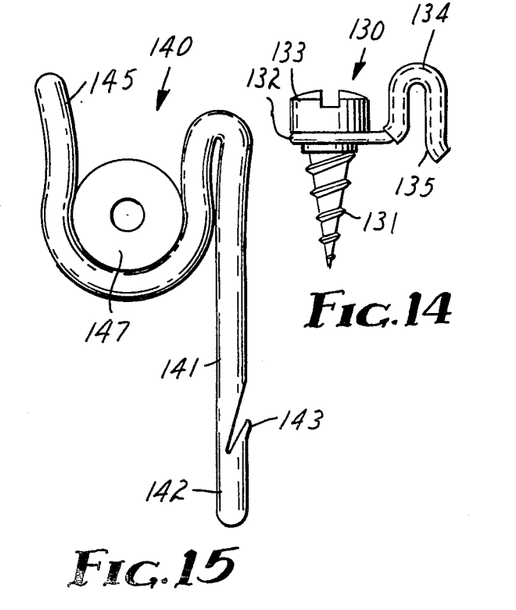
FIG. 14 is a side view of a seventh alternate embodiment of an anchor which may be used in the method according to the present invention.
FIG. 15 is a side view of an eighth alternate embodiment of an anchor which may be used in the method according to the present invention.

FIG. 14 illustrates yet a seventh alternate embodiment of an anchor 130 which may be used in the method according to the present invention. The anchor 130 comprises a conventional bone screw 131 which may be engaged in a socket in a temporal bone, and a wire having at one end a loop 132 adapted to be engaged under a head 133 of the screw 131 engaged in the socket, and a generally U-shaped portion 134 over which a resiliently elastic tube 135 is positioned so that a lead may be frictionally retained between the adjacent surfaces of the tube 135. Alternately no sleeve need be used, and the U-shaped end portion could be shaped to receive a collar over a lead like a collar 147 of an anchor 140 (FIG. 15).

FIG. 15 shows an eighth alternate embodiment of an anchor which may be used in the method according to the present invention generally designated by the reference numeral 140. The anchor 140 comprises (1) a metal wire 141 having a first end portion 142 formed with a barb 143 and adapted to be inserted in a socket in a temporal bone, and a second end portion 145 which is generally U-shaped, and (2) the resiliently elastic hollow cylindrical polymeric collar 147 adapted to be slid lengthwise over a lead with the lead in its central opening and then to be pressed into and compressed within the U-shaped second portion 145 so that the collar 147 provides a layer of resiliently elastic polymeric material over the adjacent surfaces of the wire 141 along the U-shaped end portion 145 and has adjacent surfaces spaced to receive and frictionally engage the lead therebetween to secure the lead to the anchor 140.

Figure 16:
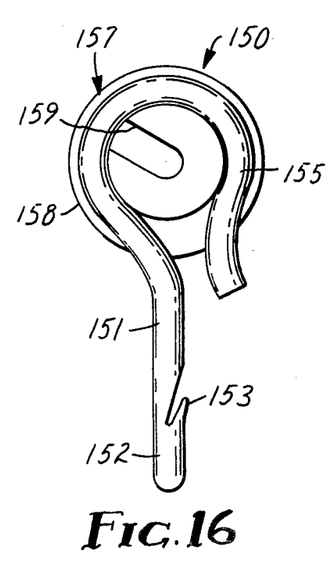
FIG. 16 is a side view of a ninth alternate embodiment of an anchor which may be used in the method according to the present invention.

FIG. 16 shows a ninth alternate embodiment of an anchor which may be used in the method according to the present invention generally designated by the reference numeral 150. The anchor 150 comprises (1) a metal wire 151 having a first end portion 152 formed with a barb 153 and adapted to be inserted in a socket in a temporal bone, and a second end portion 155 which is formed into a generally U-shaped loop, and (2) a resiliently elastic hollow cylindrical polymeric plug 157. The plug 157 has a generally cylindrical portion with a flange 158 at one end, and has an axially extending slot 159 opening through one side surface adapted to receive a lead. After the lead is positioned within the slot 159, the cylindrical portion can be pressed into the second end portion 155 of the anchor 150 which will compress the cylindrical portion of the plug 157 so that the plug 157 provides a layer of resiliently elastic polymeric material over the adjacent surfaces of the wire along the U-shaped end portion 155, and has adjacent surfaces spaced to receive and frictionally engage the lead therebetween to secure it to the wire 151.

We have now described the method according to the present invention and numerous embodiments of anchors that may be used in that method. It is apparent that other embodiments of the anchor could be used in the method such as may result by interchanging or slightly modifying parts of the various anchors described, without departing from the spirit of the present invention. Thus the scope of the present invention should not be limited by the description herein, but only by the method steps and structures recited in the dependent claims and their equivalents.

As an example concerning the anchor 26 shown in FIG. 6 and the method illustrated in FIGS. 1 through 5, some surgeons may prefer to use the side of the anchor 26 between the distal tip 42 and the temporal bone 20 with which it is engaged as a guide during positioning of a lead and electrode, and to then pull the lead between the adjacent surfaces of the tube 40 over the U-shaped end portion 30 of the anchor 26.

We claim:

1. In the method of implanting one or more electrodes in or adjacent to a human cochlea so that the electrode can afford electrical stimulation of nerve fibers to produce the sensation of sound, which method comprises the step of positioning a lead terminating at the electrode through an opening surgically made in a temporal bone with the electrode at a predetermined position relative to the cochlea, the improvement wherein said method further includes the steps of:

(a) providing an anchor having a first end portion and a second end portion comprising means for engaging a portion of the lead to restrict longitudinal, transverse and rotational movement thereof relative to the anchor, the first end portion of the anchor including a barb projecting along one side and toward the second portion of the anchor;

(b) forming a socket from the opening into the temporal bone, which socket is adapted to receive the first end portion of the anchor;

(c) inserting the first end portion of the anchor into the socket with the anchor rotated from its desired orientation;

(d) rotating the anchor to its desired orientation; and (e) engaging a portion of the lead with the means for engaging of the anchor.

2. An anchor adapted to be inserted in the temporal bone of a human skull and to be engaged with one or more leads extending to an electrode to help position the electrode at a desired location relative to the cochlea, said anchor comprising a metal wire having a first end portion of a size capable of insertion in a socket in the temporal bone and comprising means adapted to firmly engage the walls defining the socket; and an opposite generally U-shaped second end portion having adjacent surfaces; and a layer of resiliently elastic polymeric material over the adjacent surfaces of said wire along said U-shaped end portion and having adjacent surfaces, the adjacent surfaces of said layer of polymeric material being spaced to frictionally receive a portion of a said lead therebetween.

3. An anchor according to claim 2 wherein said means adapted to firmly engage the walls of the socket comprise a barb projecting along one side and toward the second end portion of the anchor.

4. An anchor according to claim 2 wherein said anchor includes a polymeric tube over said generally U-shaped second end portion to provide said layer of polymeric material.

* * * * *